United States Patent
Ueno

(10) Patent No.: US 7,854,921 B2
(45) Date of Patent: Dec. 21, 2010

(54) HAIR CARE PRODUCT

(75) Inventor: Masako Ueno, Tokyo (JP)

(73) Assignee: Kao Corporation, Tokyo (JP)

( * ) Notice: Subject to any disclaimer, the term of this patent is extended or adjusted under 35 U.S.C. 154(b) by 1347 days.

(21) Appl. No.: 10/568,411

(22) PCT Filed: Aug. 6, 2004

(86) PCT No.: PCT/JP2004/011341

§ 371 (c)(1),
(2), (4) Date: Feb. 14, 2006

(87) PCT Pub. No.: WO2005/018586

PCT Pub. Date: Mar. 3, 2005

(65) Prior Publication Data

US 2006/0165628 A1   Jul. 27, 2006

(30) Foreign Application Priority Data

Aug. 21, 2003   (JP) .............................. 2003-297633

(51) Int. Cl.
*A61Q 5/12* (2006.01)
(52) U.S. Cl. ................. 424/70.12; 424/70.28; 424/401; 424/70.1
(58) Field of Classification Search ........................ None
See application file for complete search history.

(56) References Cited

U.S. PATENT DOCUMENTS

| | | | |
|---|---|---|---|
| 5,286,476 A | 2/1994 | Nanba et al. | |
| 5,788,884 A * | 8/1998 | Kuwata et al. | ................ 516/67 |
| 5,973,066 A | 10/1999 | Sakuta et al. | |
| 6,251,379 B1 * | 6/2001 | Omura et al. | .............. 424/70.1 |

FOREIGN PATENT DOCUMENTS

| | | |
|---|---|---|
| JP | 1-113311 | 5/1989 |
| JP | 1-139522 | 6/1989 |
| JP | 1-175923 | 7/1989 |
| JP | 6-505504 | 6/1994 |
| JP | 7-69837 | 3/1995 |
| JP | 2003-512308 | 4/2003 |

OTHER PUBLICATIONS

Pharmaceutical, 1$^{st}$ ed., Jul. 1966, p. 159 (Chinese).

* cited by examiner

*Primary Examiner*—Robert A Wax
*Assistant Examiner*—Bethany Barham
(74) *Attorney, Agent, or Firm*—Oblon, Spivak, McClelland, Maier & Neustadt. L.L.P.

(57) ABSTRACT

An oil-in-water type hair cosmetic composition obtained by dispersing liquid droplets of a mixture of Components (A) and (B) and liquid droplets of a mixture of Components (A) and (C) in an aqueous phase containing an emulsifier.

A preparation process of an oil-in-water type hair cosmetic composition, which includes the following steps: (Step 1) mixing of Components (A) and (B) (preparation of a silicone mixture (AB)), (Step 2) mixing of Components (A) and (C) (preparation of a silicone mixture (AC)), (Step 3): mixing of an emulsifier, the other components and water (preparation of a base composition), and (Step 4): addition and mixing, in the base composition, the silicone mixtures (AB) and (AC) without dissolving each other (formation of liquid droplets of the silicone mixture (AB) and liquid droplets of the silicone mixture (AC) in the aqueous phase).

Component (A):

$$H_3C-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_a-\underset{\underset{CH_3}{|}}{\overset{\overset{CH_3}{|}}{Si}}-CH_3 \quad (1)$$

a: number-average polymerization degree ranging from 1,000 to 20,000

Component (B):

$$H_3C-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_b-\underset{\underset{CH_3}{|}}{\overset{\overset{CH_3}{|}}{Si}}-CH_3 \quad (2)$$

b: number-average polymerization degree ranging from 10 to 800

Component (C):

$$\left[\underset{\underset{CH_3}{|}}{\overset{\overset{CH_3}{|}}{Si}}-O\right]_c \quad (3)$$

c: number-average polymerization degree of from 3 to 7

The hair cosmetic composition of the invention is excellent in spreadability, has a slick and smooth feel, and a soft touch upon application of it to the wet hair, can impart the hair with a sleek touch without harsh friction upon rising, and can impart the hair with an unsticky smooth touch, moisturized feel and adequate manageability after drying.

20 Claims, No Drawings

HAIR CARE PRODUCT

FIELD OF THE INVENTION

The present invention relates to a hair cosmetic composition having a dimethylpolysiloxane dispersed therein and a preparation process of the composition.

BACKGROUND OF THE INVENTION

Hair coloring is very popular today. The hair is however damaged by coloring or applying a permanent wave and such hair tends to suffer from symptoms such as overly dry hair and poor manageability. Hair cosmetic compositions are therefore required to have a performance capable of imparting good smoothness and flexibility to the damaged hair during the time from wetting until drying. On the other hand, "stickiness" of the hair is undesired because it is unpleasant tactilely and visually. To give smoothness to the hair after drying, a silicone is incorporated in many hair cosmetic compositions. Incorporation of it however involves the problem that harsh friction occurs between hair strands upon rinsing. Moreover, incorporation of a silicone in an increased amount or a silicone with a high polymerization degree disturbs uniform application of the resulting composition to the hair, resulting in excessive stickiness or deteriorated gloss.

A hair treating agent using a silicone with a low polymerization degree or a volatile silicone in combination with a dimethylsilicone rubber with a high polymerization degree is known (refer to, for example, Patent document 1 and Patent document 2). The hair treating agent however involves problems in spreadability upon application, and finger combing smoothness during the time from its application to rinsing and in addition, it has poor flexibility, causes harsh friction upon rising and is sticky during drying to after drying.

Patent document 1: JP-A-1-139522
Patent document 2: JP-A-1-113311

SUMMARY OF THE INVENTION

In one aspect of the present invention, there is thus provided an oil-in-water type hair cosmetic composition obtained by dispersing, in an aqueous phase containing an emulsifier, droplets of a mixture of the below-described Components (A) and (B) and droplets of a mixture of the below-described Components (A) and (C):

(A) a dimethylpolysiloxane represented by the following formula (1):

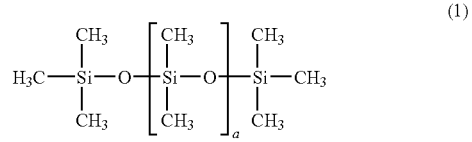

wherein, a stands for a number-average polymerization degree ranging from 1,000 to 20,000

(B) a dimethylpolysiloxane represented by the following formula (2):

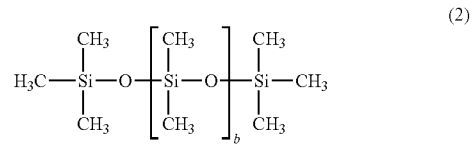

wherein, b stands for a number-average polymerization degree ranging from 10 to 800

(C) a cyclic dimethylpolysiloxane represented by the following formula (3):

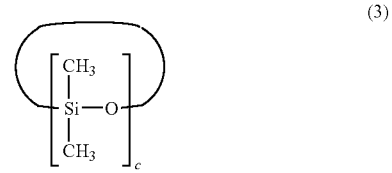

wherein, c stands for a number-average polymerization degree ranging from 3 to 7.

In another aspect of the invention, there is also provided a preparation process of an oil-in-water type hair cosmetic composition, which comprises:

Step 1: mixing Components (A) and (B) to prepare a silicone mixture (AB),

Step 2: mixing Components (A) and (C) to prepare a silicone mixture (AC),

Step 3: mixing an emulsifier, the other components to be incorporated in the hair cosmetic composition, and water to prepare a base composition, and Step 4: adding and mixing, in the base composition, the silicone mixture (AB) and the silicone mixture (AC) without dissolving each other and forming droplets of the silicone mixture (AB) and droplets of the silicone mixture (AC) in the aqueous phase of the hair cosmetic composition.

DETAILED DESCRIPTION OF THE INVENTION

The present invention relates to a hair cosmetic composition which is excellent in spreadability, smooth feel and has a supple touch upon its application to the wet hair, can impart the hair with a sleek touch without harsh friction upon rinsing, and moreover can impart the hair with a sleek touch, moist feel and adequate manageability without giving a sticky feel to the hair; and a preparation process thereof.

The present inventors have found that a hair cosmetic composition having the above-described performances can be obtained by constituting an emulsion system having, in the aqueous phase thereof, liquid droplets of a mixture of a dimethylpolysiloxane with a high polymerization degree and a dimethylpolysiloxane with a low polymerization degree and liquid droplets of a mixture of a dimethylpolysiloxane with a high polymerization dimethylpolysiloxane and a cyclic dimethylpolysiloxane existing independently.

As Component (A), a dimethylpolysiloxane with a number-average polymerization degree of from 1000 to 20000 is used. The dimethylpolysiloxane preferably has a number-average polymerization degree of from 1500 to 15000, more preferably from 1700 to 10000.

As Component (A), two or more dimethylpolysiloxanes may be used in combination. Its content in the hair cosmetic composition of the invention is preferably from 0.05 to 6 wt. %, more preferably from 0.1 to 5 wt. %, still more preferably from 0.1 to 4 wt. % from the standpoints of smooth finger combing upon application of the composition to the wet hair and upon rinsing and good manageability of the hair after drying.

As Component (B), a dimethylpolysiloxane having a number-average polymerization degree of from 10 to 800 can be used. The dimethylpolysiloxane preferably has a number-average polymerization degree of from 50 to 700, more preferably from 100 to 650.

As Component (B), two or more dimethylpolysiloxanes may be used in combination. Its content in the hair cosmetic composition of the invention is preferably from 0.1 to 10 wt. %, more preferably from 0.5 to 8 wt. %, still more preferably from 0.7 to 6 wt. % from the standpoints of avoiding harsh friction upon rinsing and imparting softness to the hair.

As Component (C), a cyclic dimethylpolysiloxane having a number-average polymerization degree of from 3 to 7 can be used. Octamethylcyclotetrasiloxane, decamethylcyclopentasiloxane and dodecamethylcyclohexasiloxane are preferred.

As Component (C), two or more cyclic dimethylpolysiloxanes may be used in combination. Its content in the hair cosmetic composition of the invention is preferably from 0.1 to 10 wt. %, more preferably from 0.5 to 8 wt. %, still more preferably from 0.7 to 6 wt. % from the standpoints of imparting a sleek touch to the hair upon rinsing and not making the hair sticky after drying.

Examples of the emulsifier to be used for the hair cosmetic composition of the invention include cationic surfactants, nonionic surfactants and amphoteric surfactants.

As the emulsifier, use of cationic surfactants is preferred because they are capable of giving a supple finish and luster to the hair. The emulsifier preferably contains a quaternary ammonium salt represented by the following formula (4), or a tertiary amine compound represented by the formula (5) or a salt thereof (which will hereinafter be called "Component (D)").

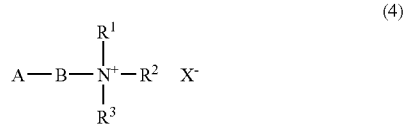

(4)

wherein, A represents a hydrogen atom or a linear or branched, saturated or unsaturated amide, N-hydrocarbon carbamoyl, acyloxy or hydrocarbon oxy group having 12 to 24 carbon atoms in total, B represents a divalent, linear or branched, saturated or unsaturated hydrocarbon group having 1 to 22 carbon atoms, at least one of $R^1$, $R^2$ and $R^3$ represents a linear or branched alkyl or alkenyl group having 1 to 24 carbon atoms in total and the remaining one or two each represents an alkyl group having 1 to 3 carbon atoms and $X^-$ represents a halide ion or organic anion.

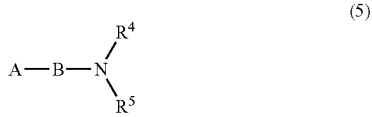

(5)

wherein, A and B have the same meanings as described above, and $R^4$ and $R^5$ each independently represents an alkyl group having 1 to 4 carbon atoms.

Examples of the quaternary ammonium salt (4) include mono(long-chain alkyl) ($C_{12-28}$) quaternary ammonium salts, di(long-chain alkyl) ($C_{12-28}$) quaternary ammonium salts, branched alkyl ($C_{12-28}$) quaternary ammonium salts, alkylamido ($C_{12-28}$) alkylene ($C_{1-5}$) quaternary ammonium salts, N-hydrocarbon ($C_{12-28}$) carbamoylalkylene ($C_{1-5}$) quaternary ammonium salts, acyl ($C_{12-28}$) oxyalkylene ($C_{1-5}$) quaternary ammonium salts, and hydrocarbon ($C_{12-28}$) oxyalkylene ($C_{1-5}$) quaternary ammonium salts.

The mono(long-chain alkyl) ($C_{12-28}$) quaternary ammonium salts include stearyltrimethylammonium chloride, myristyltrimethylammonium chloride, cetyltrimethylammonium chloride, arachyltrimethylammonium chloride, behenyltrimethylammonium chloride, lauryltrimethylammonium chloride and N-stearyl-N,N,N-tri(polyoxyethylene)ammonium chloride (3 moles added in total). The di (long-chain alkyl) ($C_{12-28}$) quaternary ammonium salts include distearyldimethylammonium chloride, dioleyldimethylammonium chloride, dipalmitylmethylhydroxyethylammonium methosulfate, diisostearyldimethylammonium methosulfate, di[(2-dodecanoylamino)ethyl]dimethylammonium chloride, and di[(2-stearoylamino)propyl]dimethylammonium ethosulfate. The branched alkyl ($C_{12-28}$) quaternary ammonium salts include 2-decyltetradecyltrimethylammonium chloride, 2-dodecylhexadecyltrimethylammonium chloride, di-2-hexyldecyldimethylammonium chloride and di-2-octyldodecyldimethylammonium chloride. The alkylamido ($C_{12}$-28) alkylene ($C_{1-5}$) quaternary ammonium salts include stearamidopropyl quaternary ammonium salts. The N-hydrocarbon ($C_{12-28}$) carbamoylalkylene ($C_{1-5}$) quaternary ammonium salts include N-stearylcarbamoylpropyl quaternary ammonium salts. The acyl ($C_{12-28}$) oxyalkylene ($C_{1-5}$) quaternary ammonium salts include stearoxypropyl quaternary ammonium salts. The hydrocarbon ($C_{12-28}$) oxyalkylene ($C_{1-5}$) quaternary ammonium salts include octadecyloxypropyltrimethylammonium chloride.

In the tertiary amine compound (5), A preferably represents an amide or hydrocarbon oxy group having 14 to 22, preferably 18 to 22 carbon atoms in total when A is other than a hydrogen atom. Its hydrocarbon moiety is preferably saturated, more preferably saturated and linear. When A is other than a hydrogen atom, B preferably represents a trimethylene group. When A represents a hydrogen atom, on the other hand, B preferably represents a $C_{18-22}$ group. A saturated group is more preferred, with a saturated and linear one being still more preferred. Examples of the group as $R^4$ or $R^5$ include methyl, ethyl, propyl, isopropyl, butyl and tert-butyl. Of these, methyl and ethyl are preferred, with methyl being more preferred. Specific preferred examples of the tertiary amine compound (5) include N,N-dimethyloctadecyloxypropylamine and stearamidopropyldimethylamine.

Salts of the tertiary amine compound (5) are formed by the neutralization of the above-described tertiary amine compound and an acidic amino acid, organic acid or inorganic acid. Examples of the acidic amino acid include glutamic acid and aspartic acid. Examples of the organic acid include carboxylic acids such as monocarboxylic acids, dicarboxylic acids, hydroxycarboxylic acids, polycarboxylic acids, alkylsulfuric acids and alkylphosphoric acids. Of these, carboxylic acids, especially dicarboxylic acids and hydroxycarboxylic acids are preferred. The dicarboxylic acids include malonic acid, succinic acid, glutaric acid, adipic acid, maleic acid, fumaric acid and phthalic acid. The hydroxycarboxylic acids include glycolic acid, lactic acid, hydroxyacrylic acid, oxybutyric acid, glyceric acid, malic acid, tartaric acid and citric acid. Examples of the inorganic acid include phosphoric acid, sulfuric acid, nitric acid and hydrochloric acid. Of these, organic acids, preferably α-hydroxycarboxylic acids, lactic acid and malic acid are preferred.

As emulsifiers other than Component (D), the following can be used. As the nonionic surfactants, polyoxyalkylene alkyl ethers, polyoxyalkylene fatty acid esters, polyoxyalkylene sorbitan fatty acid esters, polyoxyalkylene sorbitol fatty acid esters, polyoxyalkylene glycerin fatty acid esters, monoglycerides, and sorbitan fatty acid esters can be used. As the amphoteric surfactants, acetic acid betaine type, amidoacetic acid betaine type, sulfobetaine type, amidosulfobetaine type, imidazolium betaine type, amino acid type, amidoamine type, phosphobetaine type, alkylamine oxides and amidoamine oxides can be used.

As the emulsifier, two or more of the above-described emulsifiers may be used in combination. Its content in the hair cosmetic composition of the invention preferably ranges from 0.1 to 20 wt. %, more preferably from 0.5 to 15 wt. %, still more preferably from 1 to 10 wt. % in order to improve the emulsion stability. The emulsifier preferably contains Component (D) and its content in the hair cosmetic composition of the invention preferably ranges from 0.05 to 10 wt. %, more preferably from 0.1 to 8 wt. %, still more preferably from 0.1 to 7 wt. % from the viewpoints of a supple finish and luster. Supposing that the contents of Components (A), (B), (C) and (D) in the hair cosmetic composition of the invention are (A) wt. %, (B) wt. %, (C) wt. % and (D) wt. %, respectively, they preferably satisfy the following equation:

$$[(A)+(B)+(C)]/(D)=2 \text{ to } 6.$$

To the hair cosmetic composition of the invention, a higher alcohol can be added further as Component (E) in order to improve finger combing smoothness through the wet hair and give smoothness to the hair. As the higher alcohol, those having 12 to 28, more preferably 16 to 24, still more preferably 22 carbon atoms are preferred. Linear or branched, saturated or unsaturated ones are usable, of which linear alkyl alcohols are preferred.

Preferred examples of Component (E) include cetyl alcohol, stearyl alcohol, arachyl alcohol, behenyl alcohol, 2-octyldodecanol, 2-hexyldecyl alcohol, isostearyl alcohol, and carnaubyl alcohol (tetracosanol). Of these, behenyl alcohol is more preferred.

As Component (E), two or more higher alcohols can be used in combination. Its content in the hair cosmetic composition of the invention is preferably from 0.5 to 11 wt. %, more preferably from 0.8 to 11 wt. %, still more preferably from 0.9 to 11 wt. % from the standpoint of imparting sleekness and smoothness upon application of the composition to the wet hair and upon rinsing. A weight ratio of the quaternary ammonium salt or tertiary amine compound as Component (D) and the higher alcohol as Component (E) preferably falls within a range of from 1:1 to 1:5, more preferably from 1:2 to 1:4.

The hair cosmetic composition of the invention may contain, in addition to the above-described components, other components and additives ordinarily employed for hair cosmetic compositions, depending on the objectives of the composition. Examples of such components include thickeners such as hydroxyethylcellulose and carboxyvinyl polymer; oil components such as hydrocarbon oil and ester oil; humectants such as 1,3-butylene glycol, propylene glycol, glycerin, and hydrolyzed protein liquid; conditioning agents such as PEG with high polymerization degree, cationic cellulose and cationic guar gum; solubilizing agents such as polyoxyethylene alkyl ether and polyoxyethylene hydrogenated castor oil; antiseptics such as paraben, bactericides such as salicylic acid, triclosan, and piroctone olamine; pH regulators such as sodium hydroxide and potassium hydroxide; chelating agents such as EDTA salts and hydroxyethanediphosphonic acid; UV absorbers such as 2-ethylhexyl paramethoxycinnamate, oxybenzone, and 2-ethylhexyl paradimethylaminobenzoate; antioxidants such as dibutylhydroxytoluene and tocopherol acetate; and extracts from animals or plants and colorants.

The hair cosmetic composition of the invention can be prepared, for example, through the following steps 1 to 4:

Step 1: Mix Components (A) and (B) to prepare a silicone mixture (AB).

Step 2: Mix Components (A) and (C) to prepare a silicone mixture (AC).

Step 3: Mix an emulsifier, the other components to be incorporated in the hair cosmetic composition, and water to prepare a base composition.

Step 4: Add and mix, in the base composition, the silicone mixture (AB) and the silicone mixture (AC) without dissolving each other and form droplets of the silicone mixture (AB) and droplets of the silicone mixture (AC) in the aqueous phase of the hair cosmetic composition, whereby an oil-in-water type hair cosmetic composition can be prepared.

The steps 1 to 3 may be performed in any arbitrary order. The silicone mixtures obtained in Steps 1 and 2 are not only simple silicone mixtures but may be diluted with a diluent such as isoparaffin. These mixtures may each be emulsified by an emulsifier (surfactant), water and the like and the resulting emulsion may be added and mixed in the base composition in Step 4.

Examples of the specific means for adding and mixing, in the base composition, the silicone mixtures (AB) and (AC) without dissolving each other in Step 4 include the following methods:

Means 1:

A method of emulsifying each of the silicone mixture (AB) and the silicone mixture (AC) in water by using a surfactant to prepare a silicone emulsion (AB) and a silicone emulsion (AC) and then adding and mixing them in the base composition.

Means 2:

A method of adding and mixing either one of the silicone mixtures (AB) and (AC) in the base composition and emulsifying the resulting mixture, and then adding and mixing the other one and emulsifying.

Means 3:

A method of adding and mixing either one of the silicone mixtures (AB) and (AC) in a portion of the base composition and emulsifying the resulting mixture, adding and mixing the other one in the remaining portion of the base composition and emulsifying the resulting mixture, and then combining and mixing these emulsions.

Means 4:

A method of adding and mixing the silicone mixture (AB) and the silicone mixture (AC) in the base composition from respective inlets and then emulsifying the resulting mixture.

In order to give a smooth feel without harsh friction to the hair upon rinsing and smooth finger combing without stickiness to the hair after drying, the components (A) and (B) of the silicone mixture (AB) are mixed preferably at a weight ratio (A):(B) ranging from 1:1 to 1:10, more preferably from 1:1 to 1:8, while the components (A) and (C) of the silicone mixture (AC) are mixed preferably at a weight ratio (A):(C) ranging from 1:1 to 1:10, more preferably from 1:1 to 1:8.

The silicone mixture (AB) and silicone mixture (AC) are mixed preferably at a weight ratio (AB):(AC) ranging from 1:4 to 4:1, more preferably 1:3 to 3:1 in order to impart the hair after drying with the excellent smooth feel and flexibility.

The hair cosmetic composition of the invention can be provided, for example, in the form of a hair rinse, hair conditioner, hair treatment, hair pack, hair cream, conditioning mousse, hair mousse, hair spray, shampoo or leave-on treatment. Of these, it is suited for a rinse-off type such as hair rinse, hair conditioner or hair treatment.

EXAMPLES

Examples 1 to 8, and Comparative Example 1

Hair conditioners as shown in Table 1 were prepared and they were evaluated.

(Preparation Process)
Preparation of hair conditioners of Examples 1 to 4
1. Add an acid to purified water heated to 60 to 80° C. (aqueous phase).
2. Mix and melt Components (D) and (E) at 60 to 80° C. (oil phase).
3. Mix half of Component (A) with Component (B) while stirring [silicone mixture (AB)].
4. Mix the remaining half of Component (A) with Component (C) while stirring [silicone mixture (AC)].
5. Add the oil phase to the aqueous phase being stirred with a propeller (about 250 rpm for the preparation of about 1 L) and continue stirring for about 30 minutes to emulsify the mixture (base composition).
6. Add either one of the silicone mixture (AB) and silicone mixture (AC) to the base composition. After completion of mixing while stirring for 20 minutes, add the other one to the base composition, and mix them while stirring for 20 minutes.
7. Cool the reaction mixture to 30° C. while stirring and terminate the preparation.

Preparation of Hair Conditioners of Examples 5 to 8
1. Add an acid to purified water heated to 60 to 80° C. (aqueous phase).
2. Mix and melt a quaternary ammonium salt or tertiary amine and a higher alcohol at 60 to 80° C. (oil phase).
3. Mix half of Component (A) with Component (B) while stirring. After the addition of water in an amount equal to that of Component (B), and then Component (D), stir the mixture [silicone emulsion (AB)].
4. Mix the remaining half of Component (A) with Component (C) while stirring. After the addition of water in an amount equal to that of Component (C), and then Component (D), stir the mixture [silicone emulsion (AC)].
5. Add the oil phase to the aqueous phase which is being stirred with a propeller (about 250 rpm for the preparation of about 1 L) and continue stirring for about 30 minutes to emulsify the mixture.
6. Add the silicone emulsion (AB) and silicone emulsion (AC) to the base composition and mix for 30 minutes while stirring.
7. Cool the reaction mixture to 30° C. while stirring and terminate the preparation.

Preparation of a Hair Conditioner as Comparative Product 1
1. Heat purified water to 60 to 80° C. (aqueous phase).
2. Mix and melt a cationic surfactant and a higher alcohol at 60 to 80° C. (oil phase).
3. Mix Component (A), Component (B) and Component (C) under stirring [Silicone mixture (ABC)].
4. Add the oil phase to the aqueous phase being stirred with a propeller (about 250 rpm for the preparation of about 1 L) and continue stirring for about 30 minutes to emulsify the mixture.
5. Add the silicone mixture (ABC) to the emulsion and mix for 30 minutes while stirring.
6. Add the other components, cool the mixture to 30° C. while stirring, and terminate the preparation.

(Evaluation Method)
A hair bundle (20 g, 30 cm) of the female hair which had been bleached once was shampooed well with a plain shampoo (prepared using sodium polyoxyethylene (2.5) lauryl ether sulfate and diethanolamide) and then dried lightly. After application of 2 g of a hair conditioner to the resulting hair bundle, it was rinsed for 30 seconds with 6 L/min of running water of 40° C., towel-dried and then dried sufficiently for 2 to 3 minutes with hot air of a drier.

Organoleptic evaluation was done by a panel of 10 experts in accordance with the below-described criteria and the hair conditioners were ranked in accordance with the average of the scores.

(Evaluation Criteria)
Spreadability upon application to the wet hair
    4: excellent spreadability
    3: good spreadability
    2: fair spreadability
    1: not so good spreadability
    0: poor spreadability
Finger combing (smoothness) upon application to the wet hair, during rinsing and drying
    4: excellent smoothness
    3: good smoothness
    2: fair smoothness
    1: not so good smoothness
    0: poor smoothness
Friction upon rinsing
    4: no friction
    3: almost no friction
    2: not so much friction
    1: some friction
    0: much friction
Softness of the hair upon rinsing
    4: very soft
    3: soft
    2: relatively soft
    1: not so soft
    0: not soft
Stickiness of the hair during drying (when half-dried) and after drying
    4: unsticky
    3: almost unsticky
    2: not so sticky
    1: sticky
    0: very sticky
Manageability of the hair after drying
    4: excellent manageability
    3: good manageability
    2: fair manageability
    1: a little inferior in manageability
    0: poor manageability (Judging Standards)
    A: an average score of 3 or greater but not greater than 4
    B: an average score of 2 or greater but less than 3
    C: an average score of 1 or greater but less than 2
    D: an average score of 0 or greater but less than 1

TABLE 1

|  | (w.t. %) | Ex. 1 | Ex. 2 | Ex. 3 | Ex. 4 | Ex. 5 | Ex. 6 | Ex. 7 | Ex. 8 | Comp. Ex. 1 |
|---|---|---|---|---|---|---|---|---|---|---|
| (A) | Methylpolysiloxane a = 3000 | 1.5 | — | — | — | — | — | — | — | — |
|  | Methylpolysiloxane a = 2500 | — | 2 | — | — | — | — | 3 | 1 | — |
|  | Methylpolysiloxane a = 2000 | — | — | 2 | — | — | — | — | 1 | — |
|  | Methylpolysiloxane a = 1600 | — | — | — | 2 | — | 2 | — | — | — |
|  | Methylpolysiloxane a = 3700 | — | — | — | — | 4 | — | — | — | — |
|  | Methylpolysiloxane a = 6000 | — | — | — | — | — | — | — | — | 5 |
| (B) | Methylpolysiloxane b = 100 | — | — | 1 | — | — | — | — | 2 | — |
|  | Methylpolysiloxane b = 250 | — | — | — | — | — | — | — | — | 5 |
|  | Methylpolysiloxane b = 200 | 1.5 | — | — | 1 | — | — | — | — | — |
|  | Methylpolysiloxane b = 400 | — | 1 | — | — | 1 | — | 1.5 | — | — |
|  | Methylpolysiloxane b = 50 | — | — | — | — | — | 2 | — | — | — |
| (C) | Decamethylcyclopentasiloxane | 1.5 | — | 3 | 0.5 | 2 | — | 1.5 | — | — |
|  | Octamethylcyclotetrasiloxane | — | 2 | — | — | — | 1 | — | 4 | — |
|  | Dodecamethylcyclohexasiloxane | — | — | — | — | — | — | — | — | 5 |
| (D) | N,N-Dimtehyl-3-octadecyloxypropylamine | 1 | 2 | 1 | — | — | — | 3 | 2 | — |
|  | N,N-Dimethyl-3-octadecyloxypropylamine lactate | — | — | — | 0.4 | — | — | 0.5 | — | — |
|  | Stearyltrimethylammonium chloride | — | — | — | 2 | — | 1 | — | 0.3 | — |
|  | Behenyltrimethylammonium chloride | — | — | — | — | 1.5 | — | — | — | — |
|  | Dimethylbenzylammonium chloride | — | — | — | — | — | — | — | — | 3 |
| (E) | Cetanol | — | 6 | 1.5 | — | — | 4 | — | — | 0.5 |
|  | Stearyl alcohol | 3.5 | — | 2 | 6 | 5 | — | 9 | — | — |
|  | Behenyl alcohol | — | — | — | — | — | — | — | 6 | — |
| Others | Benzyloxyethanol | 0.5 | 0.2 | 0.3 | 0.5 | 0.2 | 0.4 | 0.5 | 0.3 | — |
|  | Lactic cid | 0.25 | 0.2 | — | 1 | — | 0.5 | 0.7 | 1 | — |
|  | Malic acid | — | 0.2 | — | — | 0.2 | — | — | 0.1 | — |
|  | Glycolic acid | — | 0.2 | 0.5 | 0.2 | 1.5 | — | 1.5 | 0.5 | — |
|  | Hydroxyethylcellulose | 0.2 | 0.2 | 0.2 | 0.2 | 0.2 | 0.2 | 0.2 | 0.2 | — |
|  | Self-emulsified monostearic acid glyceride | — | — | — | — | — | — | — | — | 3 |
|  | Ethylene glycol monostearate | — | — | — | — | — | — | — | — | 5 |
|  | Lanoline | — | — | — | — | — | — | — | — | 1 |
|  | Squalane | — | — | — | — | — | — | — | — | 2 |
|  | Sodium hyaluronate | — | — | — | — | — | — | — | — | 0.001 |
|  | Antiseptic | — | — | — | — | — | — | — | — | Trace |
|  | Colorant | — | — | — | — | — | — | — | — | Trace |
|  | Perfume | — | — | — | — | — | — | — | — | Trace |
|  | Purified water | Balance | Balance | Balance | Balance | Balance | Balance | Balance | Balance | Balance |
| Evaluation | Spreadability upon application to the wet hair | A | A | B | B | B | B | A | A | C |
|  | Finger combing upon application to the wet hair | A | A | A | B | B | B | A | B | D |
|  | Finger combing upon rinsing | A | A | A | A | B | B | A | A | B |
|  | Absence of harsh friction upon rinsing | B | A | B | A | B | B | A | A | C |
|  | Softness of the hair upon rinsing | A | B | A | B | A | B | A | B | D |
|  | Stickiness of the hair during drying (when the hair is half dried) | B | A | B | A | B | A | B | A | C |
|  | Stickiness of the hair after drying | B | A | A | A | B | A | A | B | C |
|  | Finger combing of the hair after drying | A | A | A | B | B | B | A | A | B |
|  | Manageability of the hair after drying | A | A | A | B | B | B | A | A | C |

The inventon claimed is:

1. An oil-in-water hair cosmetic composition comprising an aqueous phase and an emulsifier and droplets of a mixture comprising polysiloxanes consisting of Components (A) and (B) and droplets of a mixture comprising polysiloxanes consisting of Components (A') and (C):

(A) a dimethylpolysiloxane represented by the following formula (1):

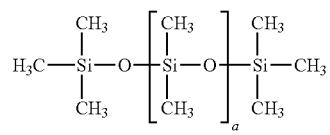

wherein, a stands for a number-average polymerization degree ranging from 1,000 to 20,000

(A') a dimethylpolysiloxane represented by the following formula (1):

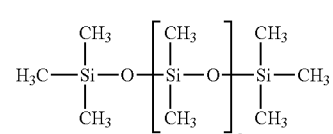

wherein, a stands for a number-average polymerization degree ranging from 1,000 to 20,000

(B) a dimethylpolysiloxane represented by the following formula (2):

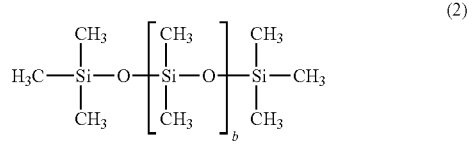

(2)

wherein, b stands for a number-average polymerization degree ranging from 10 to 800

(C) a cyclic dimethylpolysiloxane represented by the following formula (3):

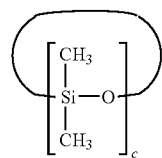

(3)

wherein, c stands for a number-average polymerization degree ranging from 3 to 7 and wherein a weight ratio of said mixture of components (A) and (B) to said mixture of components (A') and (C) is from 1:4 to 4:1.

2. The oil-in-water hair cosmetic composition of claim 1, which is prepared by the following steps 1 to 4:

Step 1: mixing Components (A) and (B) to prepare a silicone mixture (AB),

Step 2: mixing Components (A') and (C) to prepare a silicone mixture (A'C),

Step 3: mixing an emulsifier, the other components to be incorporated in the hair cosmetic composition, and water to prepare a base composition, and Step 4: adding and mixing, in the base composition, the silicone mixture (AB) and the silicone mixture (A'C) without dissolving each other and forming droplets of the silicone mixture (AB) and droplets of the silicone mixture (A'C) in the aqueous phase of the hair cosmetic composition.

3. The oil-in-water hair cosmetic composition of claim 1 or 2, wherein the emulsifier comprises Component (D):

(D) a quaternary ammonium salt represented by the following formula (4):

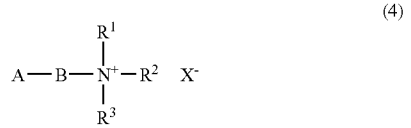

(4)

wherein, A represents a hydrogen atom or a linear or branched, saturated or unsaturated amide, N-hydrocarbon carbamoyl, acyloxy or hydrocarbon oxy group having 12 to 24 carbon atoms in total, B represents a divalent, linear or branched, saturated or unsaturated hydrocarbon group having 1 to 22 carbon atoms, at least one of $R^1$, $R^2$ and $R^3$ represents a linear or branched alkyl or alkenyl group having 1 to 24 carbon atoms in total and the remaining one or two represents an alkyl group having 1 to 3 carbon atoms and X— represents a halide ion or organic anion, or a tertiary amine compound represented by the formula:

(5)

wherein, A and B have the same meanings as described above, and $R^4$ and $R^5$ each independently represents an alkyl group having 1 to 4 carbon atoms, or salt thereof.

4. The oil-in-water hair cosmetic composition of claim 1, further comprising a higher alcohol as Component (E).

5. A preparation process of an oil-in-water hair cosmetic composition, which comprises the following steps 1 to 4:

Step 1: mixing polysiloxanes consisting of Components (A) and (B) to prepare a silicone mixture (AB), Step 2: mixing polysiloxanes consisting of Components (A') and (C) to prepare a silicone mixture (A'C), Step 3: mixing an emulsifier, the other components to be incorporated in the hair cosmetic composition, and water to prepare a base composition, and Step 4: adding and mixing, in the base composition, the silicone mixture (AB) and the silicone mixture (A'C) without dissolving each other and forming droplets of the silicone mixture (AB) and droplets of the silicone mixture (A'C) in the aqueous phase of the hair cosmetic composition, (A) a dimethylpolysiloxane represented by the following formula (1):

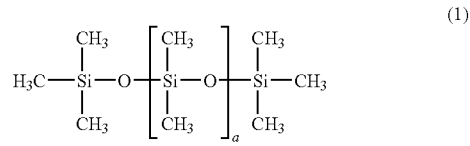

(1)

wherein, a stands for a number-average polymerization degree ranging from 1000 to 20000

(A') a dimethylpolysiloxane represented by the following formula (1):

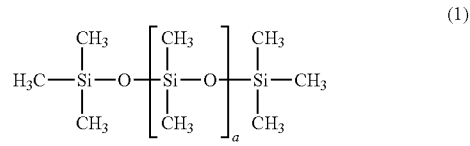

(1)

wherein, a stands for a number-average polymerization degree ranging from 1,000 to 20,000

(B) a dimethylpolysiloxane represented by the following formula (2):

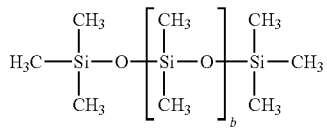
(2)

wherein, b stands for a number-average polymerization degree ranging from 10 to 800

(C) a cyclic dimethylpolysiloxane represented by the following formula (3):

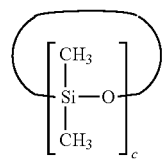
(3)

wherein, c stands for a number-average polymerization degree ranging from 3 to 7 wherein a weight ratio of said mixture of components (A) and (B) to said mixture of components (A') and (C) is from 1:4 to 4:1.

6. The oil-in-water hair cosmetic composition of claim 2, further comprising a higher alcohol as Component (E).

7. The oil-in-water hair cosmetic composition of claim 3, further comprising a higher alcohol as Component (E).

8. The oil-in-water hair cosmetic composition of claim 1, wherein said weight ratio of said mixture of Components (A) and (B) to said mixture of Components (A') and (C) is from 1:3 to 3:1.

9. The oil-in-water hair cosmetic composition of claim 1, wherein component (a) has a number-average polymerization degree of 1,500 to 15,000.

10. The oil-in-water hair cosmetic composition of claim 1, wherein composition comprises 0.5 to 6 wt. % of Component (A) +Component (A').

11. The oil-in-water hair cosmetic composition of claim 1, wherein component (b) has a number-average polymerization degree of 50 to 700.

12. The oil-in-water hair cosmetic composition of claim 1, wherein composition comprises 0.1 to 10 wt. % of Component (B).

13. The oil-in-water hair cosmetic composition of claim 1, wherein composition comprises 0.1 to 10 wt. % of Component (C).

14. The oil-in-water hair cosmetic composition of claim 1, wherein emulsifier is a cationic surfactant.

15. The oil-in-water hair cosmetic composition of claim 1, wherein said emulsifier is present in amount of 0.1 to 20 wt. %.

16. The oil-in-water hair cosmetic composition of claim 3, wherein a weight ratio of Component (A) + Component (A') +Component (B) +Component (C)/Component (D) is 2 to 6.

17. The oil-in-water hair cosmetic composition of claim 4, wherein said higher alcohol is present in an amount of from 0.8 to 11 wt. %.

18. The oil-in-water hair cosmetic composition of claim 3, further comprising a higher alcohol as component (E) wherein a weight ratio of Component (D)/Component (E) is 1:2 to 1:4.

19. The oil-in-water hair cosmetic composition of claim 1, wherein a ratio of components (A) and (B) in said mixture of components (A) and (B) is 1:1 to 1:10.

20. The oil-in-water hair cosmetic composition of claim 1, wherein a ratio of components (A') and (C) in said mixture of components (A') and (C) is 1:1 to 1:10.

* * * * *